United States Patent

Büttner et al.

[11] 4,079,090
[45] Mar. 14, 1978

[54] PREPARATION OF TRICHLOROMETHYL-TRIFLUORO METHYL-BENZENES

[75] Inventors: Gerhard Büttner, Cologne; Erich Klauke, Odenthal; Herbert Schwarz, Leverkusen; Fritz Döring, Odenthal-Gloebusch, all of Germany

[73] Assignee: Bayer Aktiengesellschaft, Leverkusen, Germany

[21] Appl. No.: 731,478

[22] Filed: Oct. 12, 1976

[30] Foreign Application Priority Data

Nov. 3, 1975 Germany .................. 2549095

[51] Int. Cl.² ............................ C07C 25/14
[52] U.S. Cl. ................................ 260/651 F
[58] Field of Search ...................... 260/651 F

[56] References Cited

U.S. PATENT DOCUMENTS

| 1,967,244 | 5/1934 | Holt et al. ............ 260/651 F |
| 2,174,512 | 10/1933 | Holt et al. ............ 260/651 F |
| 3,457,310 | 7/1969 | Fischback et al. ............ 260/578 |

FOREIGN PATENT DOCUMENTS

| 4,328,086 | 3/1968 | Japan ................... 260/651 F |
| 1,416,181 | 12/1975 | United Kingdom ........ 260/651 F |

Primary Examiner—Earl C. Thomas
Assistant Examiner—Wayne A. Langel
Attorney, Agent, or Firm—Burgess, Dinklage & Sprung

[57] ABSTRACT

A process for preparing a xylene which is fluorinated and chlorinated in the side chain, having the formula

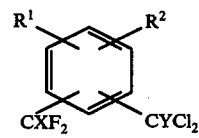

(I)

wherein
X represents hydrogen or fluorine and
Y represents hydrogen or chlorine and
$R^1$ and $R^2$ are identical or different and represent hydrogen, halogen, a trifluoromethyl or trichloromethyl group or an aliphatic or aromatic radical and
$R^1$ and $R^2$ can be bonded via hydrocarbon members to form an aromatic ring,
by contacting a compound of the formula

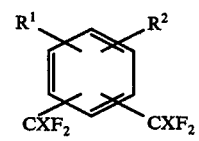

(II)

wherein X, $R^1$ and $R^2$ have the above-mentioned meanings,
with a compound of the formula

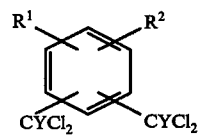

(III)

wherein X, $R^1$ and $R^2$ have the above-mentioned meanings, in the presence of a halogen transfer catalyst at elevated temperature.

23 Claims, No Drawings

PREPARATION OF TRICHLOROMETHYL-TRIFLUORO METHYL-BENZENES

The invention relates to a process for the preparation of trichloromethyl-trifluoromethyl-benzenes from xylenes in which the methyl groups are completely or partially chlorinated and from xylenes in which the methyl groups are completely or partially fluorinated.

It is known to chlorinate the trifluoromethyl group of trifluoromethylbenzene with the aid of aluminium chloride and acetyl chloride (J. amer. chem. Soc. 60, 1697 (1938)). Chlorination of m- and p-bis-(trifluoromethyl)-benzenes with the aid of aluminum chloride is known from Z. obsc. chim. 37, 1626 (1967) and with the aid of 3,5-bis-(trifluoromethyl)-nitrobenzene is known from U.S. Pat. No. 3,457,310. However, the reactions described here proceed with low yields, based on the starting compounds, and with low selectivity.

SUMMARY OF THE INVENTION

Broadly, this invention contemplates a process for preparing a xylene which is fluorinated and chlorinated in the side chain, of the formula

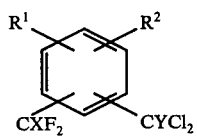
(I)

wherein
X represents hydrogen or fluorine and
Y represents hydrogen or chlorine and
$R^1$ and $R^2$ are identical or different and represent hydrogen, halogen, a trifluoromethyl or trichloromethyl group or an aliphatic or aromatic radical and
$R^1$ and $R^2$ can be bonded via hydrocarbon members to form an aromatic ring,
which comprises contacting a compound of the formula

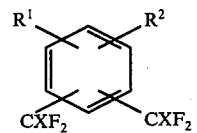
(II)

wherein X, $R^1$ and $R^2$ have the above-mentioned meanings,
with a compound of the formula

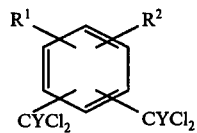
(III)

wherein X, $R^1$ and $R^2$ have the above-mentioned meanings, in the presence of a halogen transfer catalyst at an elevated temperature.

A process for the preparation of xylenes, which are fluorinated and chlorinated in the side chains, of the formula

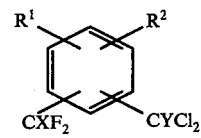
(I)

wherein
X represents hydrogen or fluorine and
Y represents hydrogen or chlorine and
$R^1$ and $R^2$ are identical or different and represent hydrogen, halogen, a trifluoromethyl or trichloromethyl group or an aliphatic or aromatic radical and
$R^1$ and $R^2$ can be bonded via hydrocarbon members to form an aromatic ring,
has now been found, in which compounds of the formula

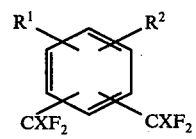
(II)

wherein X, $R^1$ and $R^2$ have the abovementioned meaning,
are reacted with compounds of the formula

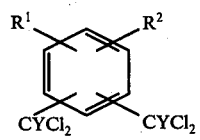
(III)

wherein Y, $R^1$ and $R^2$ have the abovementioned meaning,
in the presence of a halogen transfer catalyst and optionally of a promoter, at elevated temperature and optionally under pressure.

The process according to the invention can be illustrated by the following reaction equation for the reaction of 1,3-bis-(trichloromethyl)-benzene with 1,3-bis-(trifluoromethyl)-benzene:

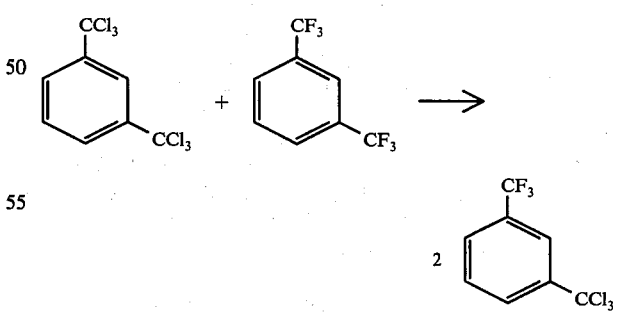

Halogens ($R^1$ and $R^2$) which may be mentioned include fluorine, chlorine and bromine, preferably fluorine and chlorine.

Optionally substituted aliphatic radicals ($R^1$ and $R^2$) can be straight-chain or branched hydrocarbon radicals with up to 18, preferably up to 12 and particularly preferentially with up to 6, carbon atoms. The following radicals may be mentioned as examples: methyl, ethyl, propyl, isopropyl, butyl, isobutyl, tert.-butyl, hexyl, nonyl, decyl, undecyl and octadecyl.

Optionally substituted aromatic radicals ($R^1$ and $R^2$) can be carbocyclic hydrocarbon radicals with 5 to 12, preferably 6 to 10, carbon atoms. The following radicals may be mentioned as examples: phenyl, naphthyl, anthracyl and diphenyl, although phenyl is preferred.

If the radicals $R^1$ and $R^2$ are bonded via hydrocarbon members to form an aromatic ring, the latter has the same scope of meanings as the abovementioned aromatic radicals. Compounds in which $R^1$ and $R^2$ are linked to form a benzene ring are particularly preferred.

Substituents of the radicals $R^1$ and $R^2$ can, in general, be all the radicals which remain unchanged under the reaction conditions. The following substituents may be mentioned as examples: halogens, preferably chlorine, $C_1$–$C_6$-alkyl groups, $C_1$–$C_6$-alkoxy groups, nitro and $C_6$–$C_{12}$-aryl groups.

Preferred compounds of the formula II are bis-(trifluoromethyl)-benzenes of the formula

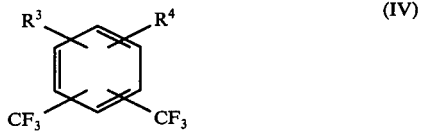

wherein $R^3$ and $R^4$ independently represent hydrogen, fluorine, chlorine, bromine and the trifluoromethyl group.

Preferred compounds of the formula III are bis-(trichloromethyl)-benzenes of the formula

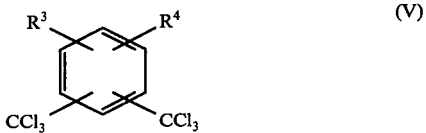

wherein $R^3$ and $R^4$ have the abovementioned meaning.

Examples of compounds of the formula II which may be mentioned are optionally substituted bis-(trifluoromethyl)-benzenes and trifluoromethyl-benzal fluorides. The preparation of these compounds is in itself known (Houben-Weyl, Volume V/3, page 84 to 395).

Examples of bis-(trifluoromethyl)-benzenes which may be mentioned are: 1,3-bis-(trifluoromethyl)-benzene, 2-chloro-1,3-bis-(trifluoromethyl)-benzene, 4-chloro-1,3-bis-(trifluoromethyl)-benzene, 5-chloro-1,3-bis-(trifluoromethyl)-benzene, 4,5-dichloro-1,3-bis-(trifluoromethyl)-benzene, 2,4,5-trichloro-1,3-bis-(trifluoromethyl)-benzene, 2-bromo-1,3-bis-(trifluoromethyl)-benzene, 4-bromo-1,3-bis-(trifluoromethyl)-benzene, 4-iodo-1,3-bis-(trifluoromethyl)-benzene, 4-fluoro-1,3-bis-(trifluoromethyl)-benzene, 1,4-bis-(trifluoromethyl)-benzene, 2-chloro-1,4-bis-(trifluoromethyl)-benzene, 2-bromo-1,4-bis-(trifluoromethyl)-benzene, 2-iodo-1,4-bis-(trifluoromethyl)-benzene, 2,5-dichloro-1,4-bis-(trifluoromethyl)-benzene, 2,5-dibromo-1,4-bis-(trifluoromethyl)-benzene, 2,3,6-tetrachloro-1,4-bis-(trifluoromethyl)-benzene, 1,3,5-tris-(trifluoromethyl)-benzene, 2-fluoro-1,3,5-tris-(trifluoromethyl)-benzene, 2-bromo-1,3,5-tris-(trifluoromethyl)-benzene and 3,4,6-trichloro-1,3,5-tris-(trifluoromethyl)-benzene.

Examples of trifluoromethyl-benzal fluorides which may be mentioned are: 2-trifluoromethyl-benzal fluoride, 2-trifluoromethyl-4-chlorobenzal fluoride and 2-trifluoromethyl-4,5-dichloro-benzal fluoride.

Examples of compounds of the formula III which may be mentioned are optionally substituted bis-(trichloromethyl)-benzenes and trichloromethyl-benzal chlorides. The preparation of these compounds is in itself known (Houben-Weyl, Volume V/3, page 735 to 750).

Examples of bis-(trichloromethyl)-benzenes which may be mentioned are: 1,3-bis-(trichloromethyl)-benzene, 2-chloro-1,3-bis-(trichloromethyl)-benzene, 4-chloro-1,3-bis-(trichloromethyl)-benzene, 5-chloro-1,3-bis-(trichloromethyl)-benzene, 4,5-dichloro-1,3-bis-(trichloromethyl)-benzene, 2,4,5-trichloro-1,3-bis-(trichloromethyl)-benzene, 2-bromo-1,3-bis-(trichloromethyl)-benzene, 4-bromo-1,3-bis-(trichloromethyl)-benzene, 4-fluoro-1,3-bis-(trichloromethyl)-benzene, 1,4-bis-(trichloromethyl)-benzene, 2-chloro-1,4-bis-(trichloromethyl)-benzene, 2-bromo-1,4-bis-(trichloromethyl)-benzene, 2,5-dichloro-1,4-bis-(trichloromethyl)-benzene, 2,5-dibromo-1,4-bis-(trichloromethyl)-benzene and 2,3,5,6-tetrachloro-1,4-bis-(trichloromethyl)-benzene. An example of a bis-(dichloromethyl)-benzene is 1,4-bis-(dichloromethyl)-benzene.

Examples of trichloromethyl-benzal chlorides which may be mentioned are: 2-trichloromethyl-benzal chloride, 2-trichloromethyl-4-chloro-benzal chloride and 2-trichloromethyl-4,5-dichloro-benzal chloride.

In general, compounds of the formula II and III which have the same type of structure and the same degree of substitution are employed for the process according to the invention. By means of this procedure, the advantageous formation of only one compound of the formula I during the reaction can be achieved. However, it is also possible to employ, as starting compounds, compounds of the formula II and III which differ in respect of their structure and substitution. Under these conditions, two compounds of the formula I are formed, which can be separated easily.

According to the process of the invention, the compounds of the formula II and III can be employed in a molar ratio of 0.3 up to 0.7 to 0.7 down to 0.3, preferably 0.4 up to 0.6 to 0.6 down to 0.4, and particularly preferentially in equivalent amounts.

Halogen transfer catalysts, such as can be employed for the process according to the invention, are in themselves known (Houben-Weyl, Volume V/3, 125 (1962)). Catalysts which can be used are, in particular, the halides of antimony, aluminum, copper, iron, titanium, tin and chromium. Examples which may be mentioned are ferric chloride, titanium tetrachloride, aluminum chloride and antimony-V halides, such as antimony pentachloride, antimony pentafluoride and antimony-V chloride fluoride, although aluminum chloride and antimony pentachloride are preferred.

In general, the halogen transfer catalysts are employed, for the process according to the invention, in amounts of 0.1 to 10 percent by weight, preferably of 0.5 to 5 percent by weight. It can be appropriate to add the total amount in two or more portions.

For the process according to the invention it can be advantageous to carry out the reaction in the presence of promoters. Promoters which may be mentioned are those compounds which form a complex anion with the catalyst or activate the latter by the formation of a complex. Examples of promoters which may be mentioned are a metal chloride, e.g. alkali metal chloride, such as sodium chloride, potassium chloride, lithium chloride, potassium fluoride or sodium fluoride, and hydrogen chloride, although hydrogen chloride is preferred.

The following catalyst/promoter combinations are particularly suitable for the process according to the invention: aluminum chloride/hydrogen chloride, antimony pentachloride/hydrogen chloride, titanium tetrachloride/hydrogen chloride, ferric chloride/hydrogen chloride and tin tetrachloride/hydrogen chloride.

The process according to the invention can be carried out at a temperature of from about 10° to about 180° C, preferably 40° to 160° C and particularly preferentially from 50° to 150° C.

The process according to the invention can be carried out under reduced pressure, normal pressure and excess pressure. Limits on the use of reduced pressure and excess pressure are imposed only by the apparatus. In general, the reaction is carried out in the pressure range of 0.5 to 200 bars, preferably 1 to 80 bars.

In general, the process according to the invention can be carried out without the use of a solvent. However, under certain circumstances it can be advantageous to carry out the reaction in the presence of a solvent or diluent; in this case, all the solvents or diluents which are suitable for carrying out Friedel-Craft reactions can be employed. Examples of preferred solvents and diluents which may be mentioned are carbon disulphide and nitrobenzene.

In general, the process according to the invention can be carried out as follows:

The starting compounds and the catalyst, optionally in a solvent or diluent, are initially introduced into a reaction vessel, optionally into an autoclave. If a promoter is to be used, this is also added at the start of the reaction. The reaction mixture is brought to the chosen reaction temperature and the chosen reaction pressure whilst stirring.

After the end of the reaction, the catalyst is either filtered off or hydrolysed with water and then filtered off. In some cases, however, it is also possible to separate off the catalyst, for example antimony pentachloride, by fractional distillation and to recycle it into the process according to the invention. The catalyst can also be removed by means of adsorbents, such as, for example, active charcoal and silica gel.

The trifluoromethyl-trichloromethyl-benzene formed can be isolated, for example, by fractional distillation.

The process according to the invention can be carried out particularly advantageously if all or part of the completely or partially fluorinated and chlorinated xylenes which do not fall within the scope of formula I and which are obtained as by-products (first runnings and residue from the fractional distillation) are re-used in the process according to the invention. High yields can be achieved by recycling the by-products.

The process according to the invention can be carried out both discontinuously and continuously.

It is surprising that trichloromethyl-trifluoromethyl-benzenes can be prepared selectively and in high yields from the chlorinated and fluorinated xylenes of the formulae II and III. This was not to be expected since it is known that trichloromethyl groups enter into condensation reactions in the presence of catalytic amounts of the halogen transfer catalysts employed here, for example aluminium chloride, (Just. Lieb. Ann. Chem. 481, 30 to 42) and trifluoromethyl groups are rechlorinated by aluminium chloride to form trichloromethyl groups (compare U.S. Patent Specification 3,457,310, J. org. chem. 26, 4713 (1961) and Z. obsc. Zhim. 37, 1626 (1967)). The trichloromethyl-trifluoromethyl-benzenes can be reacted with benzene in the presence of aluminum chloride in a Friedel-Crafts-reaction to fungicides (DOS (German Published Specification No. 1 795 249)). Moreover they are intermediates for dyestuffs (DOS (German Published Specification 2 364 475)). The trichloromethyl-trifluoromethyl-benzenes themselves have a bactericidal and fungicidal action (U.S. Pat. No. 3,457,310).

EXAMPLE 1

342 g (2.5 mols) of 1,3-bis-(trifluoromethyl)-benzene, 751 g (1.6 mols) of 1,3-bis-(trichloromethyl)-benzene and 21 g of aluminium chloride are initially introduced, at 20° C, into a 1.3 liter stirred kettle made of steel. The reaction mixture is heated to about 50° C, whilst stirring, and at the same time is saturated with hydrogen chloride. The mixture is stirred for 3 hours at this temperature and under a hydrogen chloride pressure of 1.5 bars. After letting down and cooling, the catalyst is filtered off.

The gas chromatogram of the reaction solution shows a content of 1-trichloromethyl-3-trifluoromethyl-benzene of 42%.

Fractional distillation of the reaction solution gives the following fractions:

a. 135 g of first runnings with a boiling point$_{13}$ of 23° to 85° C; the first runnings consist to the extent of 80% of 1,3-bis-(trifluoromethyl)-benzene, b. 425 g of 1-trichloromethyl-3-trifluoromethyl-benzene with a boiling point$_{13}$ of 88° to 90° C (this corresponds to a conversion of 40%) and c. 495 g of a distillation residue; the residue consists to the extent of 88% of 1,3-bis-(trichloromethyl)-benzene.

The first runnings and the distillation residue are reemployed, together with fresh 1,3-bis-(trifluoromethyl)-benzene, in the reaction. High space/time yields are achieved by the repeated cycling of the first runnings and the distillation residue.

First Cycle 751 g (2.4 mols) of 1,3-bis-(trichloromethyl)-benzene (consisting of 495 g of distillation residue and 256 g of fresh 1,3-bis-(trichloromethyl)-benzene), together with 342 g (1.6 mols) of 1,3-bis-(trifluoromethyl)-benzene (consisting of 135 g of first runnings from the distillation and 207 g of 1,3-bis-(trifluoromethyl)-benzene are initially introduced into the abovementioned 1.3 l stirred kettle made of steel. 21 g of aluminium chloride are added at 20° C and the reaction mixture is saturated with hydrogen chloride. The reaction mixture is stirred for 4 hours at 70° C and under a hydrogen chloride pressure of 1.5 bars.

The gas chromatogram of the reaction solution shows a content of 1-trichloromethyl-3-trifluoromethyl-benzene of 40.7%.

Fractional distillation of the reaction solution gives the following fractions:

a. 139 g of first runnings with a boiling point$_{13}$ of 23° to 85° C; the first runnings consist to the extent of about 80% of 1,3-bis-(trifluoromethyl)-benzene, b. 409 g of 1-trichloromethyl-3-trifluoromethyl-benzene with a boiling point$_{13}$ of 88° to 90° C (this corresponds to a conversion of 39%) and c. 513 g of a distillation residue; the residue consists to the extent of 86% of 1,3-bis-(trichloromethyl)-benzene.

Second Cycle

A further 251 g (2.4 mols) of 1,3-bis-(trichloromethyl)-benzene (consisting ... 513 g of distillation residue from the first cycle and 238 g of fresh 1,3-bis-(trichloromethyl)-benzene), together with 342 g (1.6 mols) of 1,3-bis-(trifluoromethyl)-benzene (consisting of 139 g of first runnings from the distillation of the first cycle and 203 g of fresh 1,3-bis-(trifluoromethyl)-benzene) are initially introduced into the abovementioned 1.3 l stirred kettle. 21 g of aluminium chloride are added at 20° C and the reaction mixture is saturated with hydrogen chloride. The reaction mixture is stirred for 4 hours at 70° C and under a hydrogen chloride pressure of 1.5 bars. After letting down and cooling, the catalyst is filtered off.

The gas chromatogram of the reaction solution shows a content of 1-trichloromethyl-3-trifluoromethyl-benzene of 41%.

Fractional distillation of the reaction solution gives the following fractions:

a. 133 g of first runnings with a boiling point$_{13}$ of 23° to 85° C; the first runnings consist to the extent of 78% of 1,3-bis-(trifluoromethyl)-benzene, b. 423 g of 1-trichloromethyl-3-trifluoromethyl-benzene with a boiling point$_{13}$ of 88° to 90° C (this corresponds to a conversion of 40%) and c. 508 g of a distillation residue; the residue consists to the extent of 85% of 1,3-bis-(trichloromethyl)-benzene.

It is also possible, with equal success, to employ only the first runnings and residues from the distillation, without the addition of fresh starting material of the formula II and III, in the cyclic processes. By means of such cyclic processes, according to the process of the invention, all of the starting material of the formulae II and III is converted, virtually quantitatively, into trichloromethyl-trifluoromethyl-benzene of the formula I in 2 to 3 cycles.

EXAMPLE 2

335 g (1.1 mols) of 1,3-bis-(trichloromethyl)-benzene, 192 g (0.9 mol) of 1,3-bis-(trifluoromethyl)-benzene and 25 g of sublimed iron-III chloride are initially introduced into a 0.7 liter steel autoclave and warmed to 150° C, whilst stirring. The mixture is saturated with hydrogen chloride gas during this time and is stirred for 5 hours at 150° C. After cooling and letting down, the dark solution is washed twice with dilute hydrochloric acid and with water, dried and then subjected to fractional distillation. 147 g (which corresponds to a yield of 31%) of 1-trichloromethyl-3-trifluoromethyl-benzene are obtained under 13 mm Hg and at 88° to 90° C.

EXAMPLE 3

2 ml of titanium tetrachloride are added to 156 g (0.5 mol) of 1,3-bis-(trichloromethyl)-benzene and 107 g (0.5 mol) of 1,3-bis-(trifluoromethyl)-benzene, in a 250 ml three-necked flask, and the mixture is heated to 100° C, whilst stirring and passing in hydrogen chloride. Whilst continuing to pass in hydrogen chloride, the homogeneous solution is stirred for 6 hours at 100° C. After the reaction has ended, gas-chromatographic analysis shows a content of 1-trifluoromethyl-3-trichloromethyl-benzene of 35%.

In order to remove the catalyst, the reaction solution is washed twice with dilute hydrochloric acid and then with water and dried. Fractional distillation gives 86 g (which corresponds to a yield of 33%) of 1-trifluoromethyl-3-trichloromethyl-benzene with a boiling point$_{12}$ of 87° to 90° C.

EXAMPLE 4

3.5 g of aluminium chloride are added to 59 g (0.5 mol) of 2-trifluoromethyl-benzal fluoride and 84 g (0.5 mol) of 2-trichloromethyl-benzal chloride, in a 250 ml three-necked flask. During the reaction, hydrogen chloride is passed through the reaction mixture. The reaction mixture is warmed to 120° C and stirred for 4 hours at this temperature.

After the reaction has ended, gas-chromatographic analysis shows 38% of 2-trifluoromethyl-benzal chloride and 25% of 2-fluorodichloro-benzal chloride.

After filtering off the catalyst, the mixture is subjected to fractional distillation through a column. 55 g (which corresponds to a yield of 24%) of 2-trifluoromethyl-benzal chloride are obtained at a boiling point$_{12}$ of 72° to 75° C and 36 g of 2-fluorodichloro-benzal chloride are obtained at a boiling point$_{11}$ of 125° to 127° C.

EXAMPLE 5

188 g (0.6 mol) of 1,4-bis-(trichloromethyl)-benzene and 86 g (0.4 mol) of 1,4-bis-(trifluoromethyl)-benzene and 6 g of aluminium chloride are initially introduced into a 0.7 l steel autoclave. The reaction mixture is saturated with hydrogen chloride and stirred for 5 hours at 150° C and under 7 bars.

After the reaction has ended, the reaction mixture is let down and the catalyst is filtered off. Gas-chromatographic analysis of the reaction product shows a content of 1-trichloromethyl-4-trifluoromethyl-benzene of 41%.

The reaction mixture is subjected to fractional distillation; 108 g (which corresponds to a yield of 51%) of 1-trichloromethyl-4-trifluoromethyl-benzene are obtained at a boiling point$_{14}$ of 90° to 92° C.

EXAMPLE 6

2 ml of antimony pentachloride are added to 348 g (1 mol) of 4-chloro-1,3-bis-(trichloromethyl)-benzene and 249 g (1 mol) of 4-chloro-1,3-bis-(trifluoromethyl)-benzene, in a 1 l three-necked flask. Hydrogen chloride is passed in until the solution is saturated and the solution is then stirred for 2.5 hours at 130° C under a weak stream of hydrogen chloride.

The reaction mixture is subjected to fractional distillation; 281 g (which corresponds to a yield of 47%) of 1-trifluoromethyl-5-trichloromethyl-2-chloro-benzene are isolated at a boiling point$_{12}$ of 116° C.

EXAMPLE 7

174 g of 2-chloro-1,3-bis-(trifluoromethyl)-benzene and 124.5 g of 2-chloro-1,3-bis-(trichloromethyl)-benzene are mixed in a 500 ml three-necked flask, the mixture is saturated with hydrogen chloride and 6 g of aluminum chloride are added. Whilst passing a little hydrogen chloride through the mixture, the latter is stirred for 5 hours at 140° C.

After the reaction has ended, the catalyst is filtered off and the reaction mixture is subjected to fractional distillation. 134 g (which corresponds to a yield of 45%) of 1-trifluoromethyl-2-chloro-3-trichloromethyl-benzene are obtained at a boiling point$_{12}$ of 120° to 123° C.

EXAMPLE 8

140 g (0.4 mol) of 2-chloro-1,4-bis-(trichloromethyl)-benzene, 106 g (0.4 mol) of 2-chloro-1,4-bis-(trifluoromethyl)-benzene and 5 g of aluminium chloride are initially introduced into a 0.3 l steel autoclave. The reaction mixture is saturated with hydrogen chloride, whilst stirring, and stirred for 4 hours at 140° C and under a hydrogen chloride pressure of 1.5 bars.

After the reaction has ended, the catalyst is filtered off and the reaction mixture is subjected to fractional distillation in vacuo. 120 g (which corresponds to a yield of 50%) of 1-trichloromethyl-2-chloro-4-trifluoromethyl-benzene are obtained at a boiling point$_{14}$ of 120° to 122° C.

EXAMPLE 9

96 g (0.25 mol) of 2,5-dichloro-1,4-bis-(trichloromethyl)-benzene and 71 g (0.25 mol) of 2,5-dichloro-1,3-bis-(trifluoromethyl)-benzene are stirred with 2 ml of antimony pentachloride for 5 hours at 150° C.

After the reaction has ended, the reaction mixture is subjected to fractional distillation in vacuo. 59 g (which corresponds to a yield of 36%) of 1-trichloromethyl-2,5-dichloro-4-trifluoromethyl-benzene are isolated at a boiling point$_{12}$ of 135° to 140° C.

EXAMPLE 10

5 g of aluminium chloride are added to 107 g (0.25 mol) of 1,3,5-tris-(trichloromethyl)-benzene and 71 g (0.25 mol) of 1,3,5-tris-(trifluoromethyl)-benzene, in a 250 ml three-necked flask. The reaction mixture is saturated with hydrogen chloride and stirred for 2.5 hours at 120° C and under a weak stream of hydrogen chloride.

After the reaction has ended, the catalyst is filtered off and the reaction mixture is subjected to fractional distillation in vacuo. 73 g of 1-trichloromethyl-3,5-bis-(trifluoromethyl)-benzene are isolated at a boiling point$_{13}$ of 90° to 93° C.

What is claimed is:

1. A process for preparing a xylene which is fluorinated and chlorinated in the side chain, of the formula

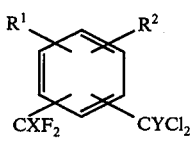

wherein

X represents hydrogen or fluorine and

Y represents hydrogen or chlorine and $R^1$ and $R^2$ are identical or different and represent hydrogen, halogen, a trifluoromethyl or trichloromethyl group or an aliphatic or aromatic radical and $R^1$ and $R^2$ can be bonded via hydrocarbon members to form an aromatic ring, which comprises contacting a compound of the formula

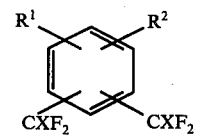

wherein X, $R^1$ and $R^2$ have the above-mentioned meanings, with a compound of the formula

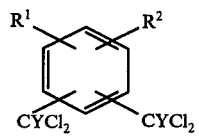

wherein Y, $R^1$ and $R^2$ have the above-mentioned meanings, in the presence of a halogen transfer catalyst at an elevated temperature.

2. A process according to claim 1 wherein said elevated temperature includes a temperature in the range of 10° to 180° C.

3. A process according to claim 2 wherein the temperature is in the range of 50° to 150° C.

4. A process according to claim 3 wherein the hydrogen transfer catalyst is selected from the group consisting of a halide of antimony, a halide of aluminum, a halide of copper, a halide of iron, a halide of titanium, a halide of tin and a halide of chromium.

5. A process according to claim 4 carried out at a pressure of 0.5 to 200 bars.

6. A process according to claim 5 wherein the process is carried out in the presence of a promoter.

7. A process according to claim 6 wherein the promoter is a compound which forms a complex anion with the catalyst.

8. A process according to claim 7 wherein the promoter is a metal chloride or a hydrogen chloride.

9. A process according to claim 8 wherein the promoter is an alkali metal chloride or hydrogen chloride.

10. A process according to claim 9 wherein the promoter is selected from the group consisting of sodium chloride, potassium chloride, lithium chloride, potassium fluoride, sodium fluoride and hydrogen fluoride.

11. A process according to claim 6 wherein the promoter is hydrogen chloride.

12. A process according to claim 6 wherein the promoter is a compound which activates the catalyst by the formation of a complex.

13. A process according to claim 5 wherein the molar ratio of the compound of the formula

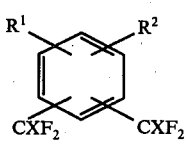

to the compound of the formula

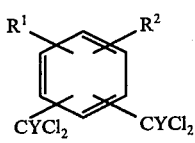

is in the range of 0.3 up to 0.7 to 0.7 down to 0.3.

14. A process according to claim 13 wherein said compounds are employed in a molar ratio of 0.4 up to 0.6 to 0.6 down to 0.4.

15. A process according to claim 13 wherein the compound having the formula

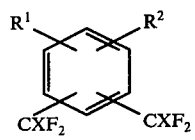

is selected from the group consisting of 1,3-bis-(trifluoromethyl)-benzene, 2-chloro-1,3-bis-(trifluoromethyl)-benzene, 4-chloro-1,3-bis-(trifluoromethyl)-benzene, 5-chloro-1,3-(trifluoromethyl)-benzene, 4,5-dichloro-1,3-bis-(trifluoromethyl)-benzene, 2,4,5-trichloro-1,3-bis-(trifluoromethyl)-benzene, 2-bromo-1,3-bis-(trifluoromethyl)-benzene, 4-bromo-1,3-bis-(trifluoromethyl)-benzene, 4-iodo-1,3-bis-(trifluoromethyl)-benzene, 4-fluoro-1,3-bis-(trifluoromethyl)-benzene, 1,4-bis-(trifluoromethyl)-benzene, 2-chloro-1,4-bis-(trifluoromethyl)-benzene, 2-bromo-1,4-bis-(trifluoromethyl)-benzene, 2-iodo-1,4-bis-(trifluoromethyl)-benzene, 2,5-dichloro-1,4-bis-(trifluoromethyl)-benzene, 2,5-dibromo-1,4-bis-(trifluoromethyl)-benzene, 2,3,6-tetrachloro-1,4-bis-(trifluoromethyl)-benzene, 1,3,5-tris-(trifluoromethyl)-benzene, 2-fluoro-1,3,5-tris-(trifluoromethyl)-benzene, 2-bromo-1,3,5-tris-(trifluoromethyl)-benzene and 3,4,6-trichloro-1,3,5-tris-(trifluoromethyl)-benzene.

16. A process according to claim 13 wherein the compound of the formula

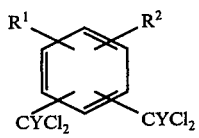

is selected from the group consisting of 1,3-bis-(trichloromethyl)-benzene, 2-chloro-1,3-bis(trichloromethyl)-benzene, 4-chloro-1,3-bis-(trichloromethyl)-benzene, 5-chloro-1,3-bis-(trichloromethyl)-benzene, 4,5-dichloro-1,3-bis-(trichloromethyl)-benzene, 2,4,5-trichloro-1,3-bis-(trichloromethyl)-benzene, 2-bromo-1,3-bis-(trichloromethyl)-benzene, 4-bromo-1,3-bis-(trichloromethyl)-benzene, 4-fluoro-1,3-bis-(trichloromethyl)-benzene, 1,4-bis-(trichloromethyl)-benzene, 2-chloro-1,4-bis-(trichloromethyl)-benzene, 2-bromo-1,4-bis-(trichloromethyl)-benzene, 2,5-dichloro-1,4-bis-(trichloromethyl)-benzene, 2,5-dibromo-1,4-bis-(trichloromethyl)-benzene, 2,3,5,6-tetrachloro-1,4-bis-(trichloromethyl)-benzene and 1,4-bis-(dichloromethyl)-benzene.

17. A process according to claim 13 wherein a trifluoromethyl benzal fluoride is reacted with the compound of the formula

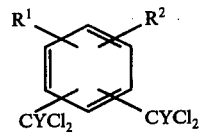

18. A process according to claim 13 wherein a trichloromethyl benzal chloride is reacted with a compound of the formula

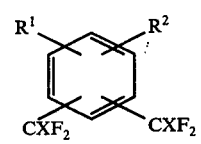

19. A process according to claim 13 wherein the reaction is carried out in the presence of a hydrogen transfer catalyst and promoter selected from the group consisting of aluminum chloride/hydrogen chloride, antimony pentachloride/hydrogen chloride, titanium tetrachloride/hydrogen chloride, ferric chloride/hydrogen chloride and tin tetrachloride/hydrogen chloride.

20. A process according to claim 5 wherein the pressure is between 1 and 80 bars.

21. A process according to claim 4 wherein said hydrogen transfer catalyst is selected from the group consisting of ferric chloride, titanium tetrachloride, aluminum chloride and an antimony V halide.

22. A process according to claim 21 wherein the hydrogen transfer catalyst is an antimony V halide selected from the group consisting of antimony pentachloride, antimony pentafluoride, antimony V chloride 23. A process for preparing a xylene which is fluorinated and chlorinated in the side chain, of the formula

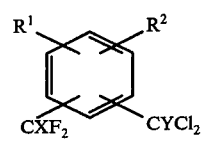

wherein
X represents hydrogen or fluorine and
Y represents hydrogen or chlorine and
R¹ and R² are identical or different and represent hydrogen, halogen, a trifluoromethyl or trichloromethyl group or an aliphatic or aromatic radical and
R¹ and R² can be bonded via hydrocarbon members to form an aromatic ring,
which comprises contacting a compound of the formula

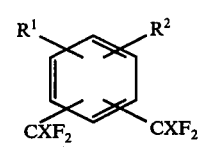

wherein X, R¹ and R² have the above-mentioned meanings,
with a compound of the formula

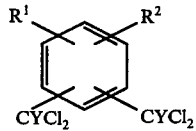
(III)
wherein Y, R¹ and R² have the above-mentioned meanings,
in the presence of a halogen transfer catalyst selected from the group consisting of a halide of antimony, a halide of aluminum, a halide of copper, a halide of iron, a halide of titanium, a halide of tin and a halide of chromium at a temperature in the range of 10° to 180° C.
* * * * *